US011995568B2

(12) United States Patent
Toubiana et al.

(10) Patent No.: US 11,995,568 B2
(45) Date of Patent: May 28, 2024

(54) IDENTIFICATION AND PREDICTION OF METABOLIC PATHWAYS FROM CORRELATION-BASED METABOLITE NETWORKS (71) Applicant: B. G. NEGEV TECHNOLOGIES AND APPLICATIONS LTD., AT BEN-GURION UNIVERSITY, Beer Sheva (IL)

(72) Inventors: David Toubiana, Beer Sheva (IL); Rami Puzis, Ashdod (IL); Yuval Elovici, Moshav Arugot (IL)

(73) Assignee: B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 815 days.

(21) Appl. No.: 17/055,906

(22) PCT Filed: May 16, 2019

(86) PCT No.: PCT/IL2019/050557
§ 371 (c)(1),
(2) Date: Nov. 16, 2020

(87) PCT Pub. No.: WO2019/220445
PCT Pub. Date: Nov. 21, 2019

(65) Prior Publication Data
US 2021/0192370 A1 Jun. 24, 2021

Related U.S. Application Data (60) Provisional application No. 62/672,075, filed on May 16, 2018.

(51) Int. Cl.
G06N 5/04 (2023.01)
G06N 20/20 (2019.01)
(Continued)

(52) U.S. Cl.
CPC ............... *G06N 5/04* (2013.01); *G06N 20/20* (2019.01); *G16B 40/00* (2019.02); *G06N 5/01* (2023.01)

(58) Field of Classification Search
CPC . G06N 5/04; G06N 20/20; G06N 5/01; G16B 40/00
See application file for complete search history.

(56) References Cited

U.S. PATENT DOCUMENTS

2009/0061422 A1* 3/2009 Linke ................... G16B 40/00
703/11
2014/0129152 A1* 5/2014 Beer ..................... G16B 20/20
702/19

FOREIGN PATENT DOCUMENTS

WO  WO-2006116622 A2 * 11/2006 ........... C12Q 1/6883
WO  WO-2018024748 A1 *  2/2018 ......... G01N 33/5767
WO  WO-2018027176 A1 *  2/2018 ......... C12N 15/1093

OTHER PUBLICATIONS

Dale .et al.; "Machine learning methods for metabolic pathway prediction" BMC bioinformatics, 11.1: 15 .pp 1-14.(2010).
(Continued)

*Primary Examiner* — Shahid K Khan
(74) *Attorney, Agent, or Firm* — BROWDY AND NEIMARK, P.L.L.C.

(57) ABSTRACT

A method and a system are provided for determining a likelihood of a metabolic pathway existing in an organism, including: calculating a feature vector for each metabolic pathway of metabolic pathways known to exist and not known to exist in the organism, wherein elements of the feature vectors are network properties of the metabolic pathways mapped to a metabolite concentration correlation network (CN); training a supervised machine learning model for classifying metabolic pathways as existing or not existing in the organism, according to the known and unknown (Continued)

feature vectors; determining, based on mapping to the CN, a feature vector of a proposed metabolic pathway, and feeding the feature vector of the proposed metabolic pathway to the trained SML model, to determine a likelihood of the proposed metabolic pathway existing in the organism.

9 Claims, 2 Drawing Sheets

(51) Int. Cl.
*G16B 40/00* (2019.01)
*G06N 5/01* (2023.01)

(56) References Cited

OTHER PUBLICATIONS

Thiele et al; "A protocol for generating a high-quality genome-scale metabolic reconstruction," Nature Protocols 5, pp. 93-121 (2010).
Monk et al; "Optimizing genome-scale network reconstructions," Nature Biotechnology 32, pp. 447-452. (2014).
Toubiana, et al., "Network analysis: tackling complex data to study plant metabolism," Trends in biotechnology 31, pp. 29-36. (2013).
Hochberg, et al., "Metabolite profiling and network analysis reveal coordinated changes in grapevine water stress response," BMC Plant Biology, 13, 84, (2013).
Gibon, et al., "Integration of metabolite with transcript and enzyme activity profiling during diurnal cycles in *Arabidopsis rosettes*," Genome Biology 7(8):23 (2006).
Toubiana, et al., "Combined correlation-based network and mQTL analyses efficiently identified loci for branched-chain amino acid, serine to threonine, and proline metabolism in tomato seeds," Plant Journal, 81(1):pp. 121-133. (2015).
Toubiana, et al., "Metabolic profiling of a mapping population exposes new insights in the regulation of seed metabolism and seed, fruit, and plant relations," PLOS Genetics. (2012).
Fire, et al., "Computationally Efficient Link Prediction in a Variety of Social Networks," Acm Transactions on Intelligent Systems and Technology 5. (2013).
Hall, M. et al. The WEKA Data Mining Software: An Update. SIGKDD Explorations 11. (2009).
Roessner-Tunali, U. ,"Metabolic Profiling of Transgenic Tomato Plants Overexpressing Hexokinase Reveals That the Influence of Hexose Phosphorylation Diminishes during Fruit Development", Plant Physiology, vol. 133, pp. 84-99 (2003).

* cited by examiner

IDENTIFICATION AND PREDICTION OF METABOLIC PATHWAYS FROM CORRELATION-BASED METABOLITE NETWORKS

FIELD OF THE INVENTION

The present invention relates to the field of information technology adapted for modeling systems biology, and in particular for classifying metabolic pathways.

BACKGROUND

The identification and understanding of metabolic pathways is a key aspect of research in fields such as crop improvement and drug design. However, the identification of metabolic pathways (MPs) is a complex process based on a constraint-based, bottom-up approach; such identification typically uses gene annotation and ontology, computational derivation, and discrete manual curation. This process is described by Thiele and Palsson in "A protocol for generating a high-quality genome-scale metabolic reconstruction," Nature Protocols 5, 93-121 (2010). Manual curation typically requires a priori knowledge of the stoichiometry between compounds, thermodynamic information of the pathway's reactome, as well as its cellular compartmentalization, and other factors. Due to the complexity of the process, metabolic pathways and their regulating enzymes are often predicted based solely on gene ontology rather than on substantial experimental evidence.

The reconstruction of metabolic pathway networks follows a defined set of steps; initiated at the known biochemistry, genomics, and physiology, followed by the governing of the physico-chemical constraints, followed by flux distribution predictions, and finalized by the determination of which of the offered solutions translate into meaningful physiological states. Regardless of whether or not they are fully validated, MPs are represented in genome-scale databases, such as: PlantCyc (http://www.plantcyc.org), BioCyc (http://biocyc.org), KEGG (http://www.genome.jp/kegg). PlantCyc is a collection of metabolic pathways found in plants. TomatoCyc is a subset of PlantCyc containing metabolic pathways known to exist in tomato plants. Some additional metabolic pathways of tomato may be in PlantCyc, but have yet to be identified. Genome-scale MP databases capture substrate-product relationships. However, the schematically represented boundaries between series of biochemical reactions neglect the crosstalk and concerted regulation between biochemically distant pathways. Moreover, metabolic pathway networks are reconstructed based on the assumption of a condition-specific, steady-state metabolic flux distribution, as described by Monk, J., Nogales, J. & Palsson, B. O., "Optimizing genome-scale network reconstructions," Nature Biotechnology 32, 447-452 (2014). This assumption does not account for endogenous or exogenous cues or factors, which may influence metabolic ties.

As opposed to the constraint-based approach of creating metabolic pathway networks, metabolite concentration correlation networks (CNs), also referred to herein simply as metabolite networks, provide a means for studying coordinated behavior of metabolites without the need for a priori knowledge. Profiles of metabolite concentrations are generated by high-throughput platforms, such as gas or liquid chromatography coupled to mass-spectrometry (GC, LC-MS), or nuclear magnetic resonance. The concentration profiles of multiple metabolites are correlated based on mathematically defined (dis-)similarity measures, which are subsequently transformed into a network form, where nodes represent the metabolites and the links between them the correlation coefficients. The usage of mathematically defined (dis-)similarity measures for metabolite correlation network analysis is described in Toubiana, et al., "Network analysis: tackling complex data to study plant metabolism," Trends in biotechnology 31, 29-36 (2013). The correlation coefficients generated and their corresponding p-values are subsequently subjected to threshold tests, removing spurious correlations. The remaining correlations are eventually transformed into network form, as described above. The resulting network illustrates a holistic view of metabolite relationships, reflecting the state of coordinated behavior at the time of sampling. For example, a correlation-based network (CN) approach was applied to metabolite concentration profiles of leaves of two grapevine cultivars to investigate the effects of different water stress regimes, as described by Hochberg, et al., "Metabolite profiling and network analysis reveal coordinated changes in grapevine water stress response," BMC Plant Biology, 13, 84, (2013).

Metabolite CNs are often reconstructed based on the exploitation of the natural variability of mapping populations or collections of different varieties or cultivars, as the multiple collections provide a large sample size, which stabilizes the correlation and reduces the error rate. CNs of metabolite concentration profiles can be combined with data of other cellular components as their relations are established based on (dis-)similarity measurements and not complex biological processes; an example is provided by Gibon, et al., "Integration of metabolite with transcript and enzyme activity profiling during diurnal cycles in *Arabidopsis* rosettes," Genome Biology 7(8):23 (2006), who studied metabolite data coupled with transcript and enzyme activity profiles to examine diurnal cycles in *Arabidopsis* rosettes. Structural properties of graphs can be used to interpret metabolite networks and to propose hypotheses. For instance, a network property analysis has been performed to identify loci regulating branched-chain amino acids in tomato seeds, as described in Toubiana, et al., "Combined correlation-based network and mQTL analyses efficiently identified loci for branched-chain amino acid, serine to threonine, and proline metabolism in tomato seeds," Plant Journal, 81(1):121-133 (2015). Community detection algorithms have also been applied to CNs to identify groups of nodes with similar chemical properties, referred to as modules, as described by Toubiana et al., "Trends in Biotechnology," cited above.

SUMMARY

An aim of the present invention is to provide a system and method for identifying metabolic pathways from metabolite concentration correlation networks (CNs). Correlation-based network analysis (CNA) and machine learning methods were adapted to predict metabolic pathways in correlation networks created from metabolite profiles of the pericarp of a tomato introgression line population. The method maps existing metabolic pathways (MPs) onto a metabolite correlation network (CN), followed by computation of a set of network properties (i.e., features) for each pathway, so as to derive a machine learning model of metabolic pathway mapping. The resulting machine learning model is then used to predict the existence of previously unidentified metabolic pathways.

There is therefore provided, by embodiments of the present invention, a method for determining a likelihood of a metabolic pathway existing in an organism, implemented by a computer processor having an associated memory, the memory including instructions that when executed by the computer processor implement steps of the method including: calculating a pathway feature vector for each metabolic pathway of first and second sets of metabolic pathways; receiving the pathway feature vectors of the first and second sets of metabolic pathways at a supervised machine learning (SML) model to train the SML model for classifying metabolic pathways as existing or not existing in the organism; mapping a proposed metabolic pathway to the CN to determine a pathway feature vector of the proposed metabolic pathway; and processing the pathway feature vector of the proposed metabolic pathway, by the trained SML model (i.e., "feeding" the pathway feature vector of the proposed metabolic pathway to the trained SML model), to determine a likelihood of the proposed metabolic pathway existing in the organism. In some embodiments, the first set of metabolic pathways is composed of metabolic pathways known to exist in the organism, wherein the second set is composed of metabolic pathways not known to exist in the organism. Elements of the pathway feature vectors are network properties of the metabolic pathways mapped to a metabolite concentration correlation network (CN). The known pathway feature vectors indicate metabolic pathways existing in the organism and the unknown pathway feature vectors indicate pathways not existing in the organism. The proposed metabolic pathway is a metabolic pathway not known to exist in the organism.

In some embodiments, the method further includes setting a model threshold of the SML model, such that the likelihood of the proposed metabolic pathway existing in the organism is positive when the SML model indicates a prediction value above the threshold, and the likelihood is negative when the SML model indicates a prediction value below the threshold.

Further embodiments may include the additional step of performing in vivo testing of the proposed metabolic pathway when the likelihood of the proposed metabolic pathway existing in the organism is positive.

Training the SML model may also include training on at least two machine learning models and selecting a model that provides results having the greatest area under a receiver operating characteristic curve (AUC). The at least two machine learning models comprise at least one algorithm from a set including: random forest (RF), random forest with reduced feature set (RF red), AdaBoost (AB), XGBoost, random tree (RT), support vector machine (SVM), and naïve Bayes (nB) algorithms.

In further embodiments the pathway feature vectors include at least 20 of the features listed in Table 1 of the specification, hereinbelow.

Training the SML model may include applying the pathway feature vectors of the first and second sets of metabolic pathways to train a first SML model, determining a subset of features of the feature vectors that most contribute to the classifying capability of the first SML model, and training a second SML model by applying pathway feature vectors of the first and second sets that include only the subset of features determined to contribute the most to the classifying capability. In some embodiments, the subset of features are the features listed in Table 2 of the specification, hereinbelow.

In embodiments of the present invention, there is further provided a system for identifying previously unknown metabolic pathways in an organism, comprising a computer processor and an associated memory, the memory comprising instructions that when executed by the computer processor implement steps including: calculating a pathway feature vector for each metabolic pathway of first and second sets of metabolic pathways; receiving the pathway feature vectors of the first and second sets of metabolic pathways at a supervised machine learning (SML) model to train the SML model for classifying metabolic pathways as existing or not existing in the organism; mapping a proposed metabolic pathway to the CN to determine a pathway feature vector of the proposed metabolic pathway; and processing the pathway feature vector of the proposed metabolic pathway, by the trained SML model, to determine a likelihood of the proposed metabolic pathway existing in the organism. In some embodiments, the first set of metabolic pathways is composed of metabolic pathways known to exist in the organism, wherein the second set is composed of metabolic pathways not known to exist in the organism.

BRIEF DESCRIPTION OF DRAWINGS

For a better understanding of various embodiments of the invention and to show how the same may be carried into effect, reference will now be made, by way of example, to the accompanying drawings. Structural details of the invention are shown to provide a fundamental understanding of the invention, the description, taken with the drawings, making apparent to those skilled in the art how the several forms of the invention may be embodied in practice.

DETAILED DESCRIPTION

Figure 1:
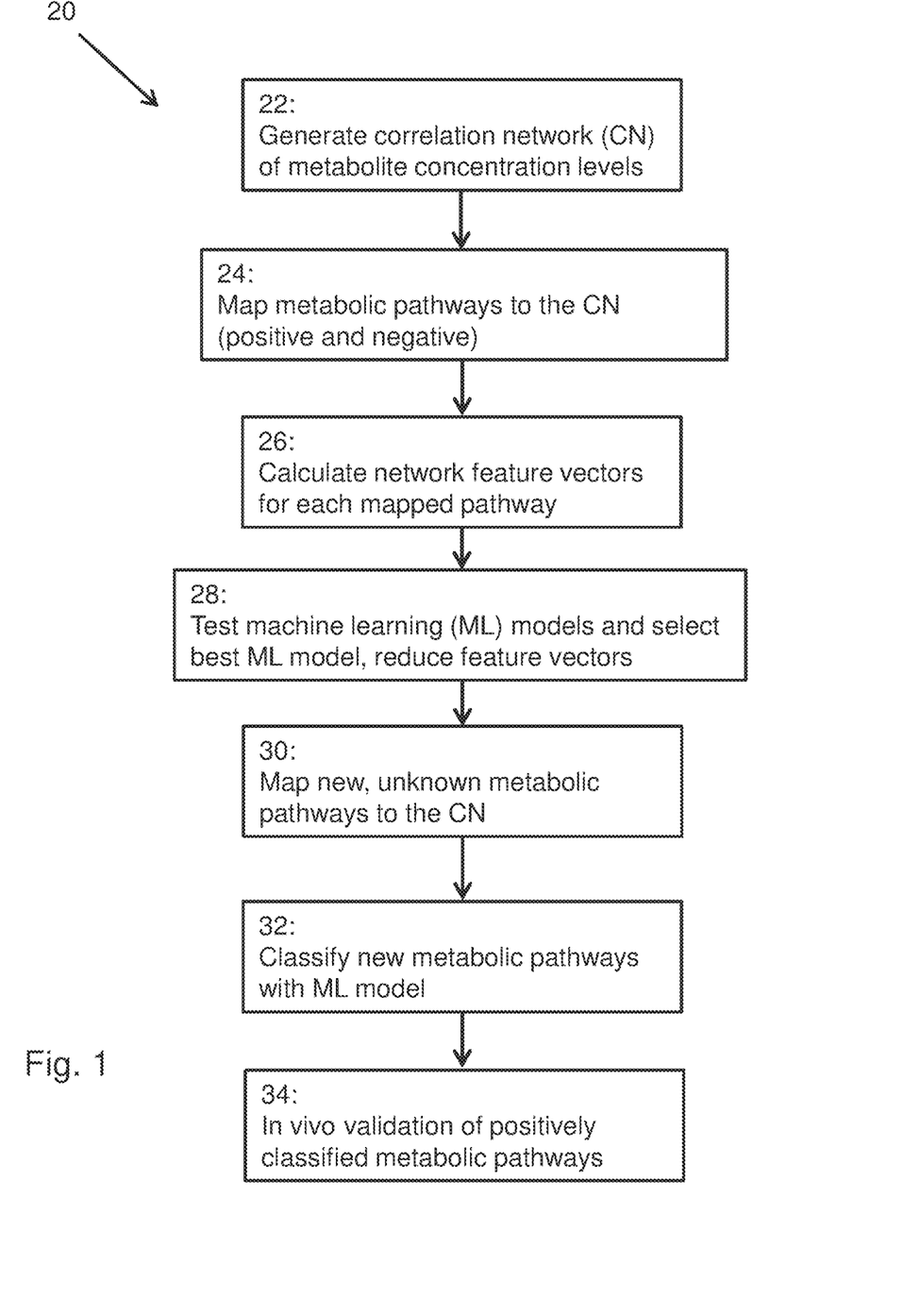
FIG. 1 is a flow diagram, depicting a process of detecting unknown metabolic pathways, according to some embodiments of the present invention.

A workflow of the methodology applied here is presented in FIG. 1, which shows a process 20 for detecting metabolic pathways previously not known to exist in an organism, according to some embodiments of the present invention. Methods described herein used supervised machine learning techniques combined with metabolite CNA. Being based on quantitative measurements of metabolites, the CNA approach effectively accounts for post-transcriptional and post-translational events, circumventing the need for gene data integration. The process disclosed herein was applied in the identification of metabolic pathways within the tomato pericarp, as described further hereinbelow.

Steps of the process 20 are as follows. A metabolite concentration CN is generated for a given organism (step 22). Next, known metabolic pathways for the organism are mapped to the CN, to create a set of "positive" CN subgraphs, and a set of metabolic pathways known to not be present in the organism, and/or random sets of metabolites, are mapped to the CN, to create a set of "negative" CN subgraphs (step 24). For each of the positive and negative instances of subgraphs, respective positive and negative vectors of network features are calculated (step 26). Network features are various features of network topology described further hereinbelow. In an application of the process describe below, feature vectors of the mapped metabolic pathways (also referred to herein as "pathway feature vectors") were generated with 148 network features for each of three CN networks (i.e., 444 features in total).

Multiple supervised machine learning models are then trained on the positive and negative pathway feature vectors, and k-fold cross validation is applied to determine a "working model" that is best able to differentiate between the positive and negative instances (step 28). Given the working model, the vectors may also be refined to include only the features that contribute the most to classification. Finally, a new set of pathways (i.e., "proposed" pathways), which may come from metabolic pathway databases, are mapped onto the CN, followed by computation of the feature vectors for the proposed pathways (step 30). The resulting feature vectors of the proposed pathways are then processed by the working model to be classified as either positive or negative, by comparing the prediction value result providing by the working model to a given threshold level (step 32). Proposed metabolic pathways scoring a prediction value greater than the threshold were classified as positively predicted (i.e., likely to exist in the organism). The threshold may be set to indicate that metabolic pathways that are positively predicted warrant further in vivo testing to confirm the existence of the metabolic pathway in the target organism (step 34).

Process 20 was applied by the inventors in a study to identify previously unknown metabolic pathways in tomato pericarp. A machine learning model generated in the study (hereinbelow, the "tomato pericarp study") identified metabolic pathways likely to exist in the tomato pericarp, including the following pathways: β-alanine-degradation-I, tryptophan-degradation-VII-via-indole-3-pyruvate (yet unknown in plants), β-alanine-biosynthesis-III, and melibiose degradation. The melibiose degradation pathway was identified, even though melibiose was NOT among the metabolites used to generate the CNs. In vivo assays validated the presence of the melibiose-degradation pathway in the tomato pericarp.

Details of the application of process 20, in particular for the study of metabolic pathways in tomato pericarp, are described in the following sections.

Generation of Metabolite Concentration CNs

General principles of generating metabolite CNs, using a pipeline for CN construction, are described by Toubiana, et al., "Network analysis: tackling complex data to study plant metabolism," *Trends in Biotechnology* 31, 29-36, 2013 [Toubiana (2013)]. Metabolite CNs are represented as weighted networks $G_i=(V_i,E_i,w)$, where $V_i$ is the set of nodes corresponding to metabolites found in the dataset of season i, E is the set of links between them, and link weights (w:E→R) correspond to the Pearson correlation coefficient. (Hereinbelow, the terms nodes and metabolites are used interchangeably.)

Metabolite concentration profiles from tomato pericarp, for three different harvesting seasons, were generated by Schauer, et al., "Comprehensive metabolic profiling and phenotyping of interspecific introgression lines for tomato improvement." Toubiana, et al., "Metabolic profiling of a mapping population exposes new insights in the regulation of seed metabolism and seed, fruit, and plant relations," *PLOS Genetics*, 8,3:e1002612, 2012 [Toubiana (2012)] constructed, for the three seasons analyzed by Schauer, weighted CNs, which were used in the application of the present invention described here. For the CNs constructed by Toubiana (2012), network links were weighted according to their correlation coefficient, allowing negative values. Spurious correlations, where $|r|\leq 0.3$ and $p\geq 0.01$, were removed. The CN for season I included 75 nodes, corresponding to the 75 metabolites, and 473 links; the CN for the season II was composed of 75 nodes and 869 links, while the CN for season III had 78 nodes and 338 links. A numeric feature profile was computed for each group of nodes in each CN, as described further hereinbelow.

Mapping Metabolic Pathways to CNs

In total, the three seasons and the corresponding CNs contained 109 different metabolites, i.e. nodes, while 52 common metabolites were contained in all three CNs. Out of the 589 MPs listed in TomatoCyc, 169 pathways were identified that shared at least two compounds with the 52 common metabolites. Each of these 169 pathways was mapped as a subgraph onto the three CNs. The mapping was partial in a sense that it omitted compounds from the pathways that were not found in the 52 common metabolites. The super-pathway of lysine, threonine, and methionine biosynthesis II, had 36% of its compounds within the networks, which resulted in the largest of all subgraphs. In total, 67 pathways were represented by exactly two compounds, while for three pathways all of their compounds were found in the CNs.

The same analysis was repeated for the remaining 625 non-tomato plant pathways, identifying 33 pathways that shared at least two compounds with the tomato metabolite CNs. For the non-plant MetaCyc pathways, 151 pathways were identified that shared at least two or more compounds with the CNs. In both cases (tomato and non-tomato MPs), the largest number of compounds shared with the CNs was 18.

For the pathways corresponding to the TomatoCyc dataset, the largest relative frequency of ~25% was observed at approximately 40% coverage, while for the pathways corresponding to the remaining PlantCyc and MetaCyc datasets the peak was reached at approximately 20% relative coverage with ~22% and ~31% relative frequency, respectively. To compare the relative distributions of coverage, a two-sided Kolmogorov-Smirnov test was employed, revealing that the PlantCyc vis-à-vis the TomatoCyc distributions, and the PlantCyc vis-à-vis the MetaCyc distributions, were statistically equal (p-values 0.09681 and 0.09887 respectively), while the TomatoCyc vis-à-vis the MetaCyc distribution was significantly different (p-value 2.631e-06).

Calculating Vectors of Network Features

In order to develop a machine learning classifier to predict previously unidentified pathways, a set of 148 different features of network properties were defined (listed in Table 1, below). Network-based features reflect a range of topological aspects of the network, as described in the following paragraphs.

One group of features that may be incorporated in the features vectors are based on structural properties that quantify the importance of nodes and describe their location within the network. These features include: number of neighbors, weighted degree, closeness centrality, betweenness centrality, stress centrality, and clustering coefficient. The edge betweenness centrality was used to quantify the importance of links, as described in Newman, M. O. & University Press, *Networks: An Introduction,* 2009. Structural properties for quantifying the relations between node pairs were geodesic distance, Jaccard coefficient, preferential attachment score, and friends measure, as described in Fire, M. et al., "Computationally Efficient Link Prediction in a Variety of Social Networks," *Acm Transactions on Intelligent Systems and Technology* 5 (2013). All of these properties were aggregated to produce features based on the sum, the mean, and the three central moments.

Next, various community detection algorithms were applied to each CN, and features were computed based on the resulting communities (i.e., densely connected clusters of nodes). Community detection algorithms were described by Newman, M. E. J. & Girvan, M, "Finding and evaluating community structure in networks," *Physical Review E,* 69 (2004).

A set of communities may be denoted as $C_i = \{C_i^1, C_i^2, \ldots, C_i^k, \ldots\}$ where k is the index of a community in a CN of season i. A pathway j can be represented as a subset of metabolites in the CN of season i, denoted as $S_i^j \subseteq V_i$. Dispersion of metabolites across the various clusters may indicate the existence or absence of the respective chemical reactions. Therefore, an additional feature included in the list of features is the ratio of the metabolites of a pathway co-residing in the largest community: $MAX_k\{|C_i^k \cap S_i^j|/|S_i^j|\}$.

Next, structural features from the neighborhoods of each pathway were computed. A neighborhood of the node v in the CN for season i is denoted as: $\Gamma_i(v) = \{u: (v, u) \in E_i\}$. Note that $\Gamma_i(v)$ is the set of all metabolites that are significantly correlated with v. Various features from the neighborhoods of nodes in each pathway were computed as follows:

Intersection: $I_i^j = |\cap_{u \in S_i^j} \Gamma_i(u)|$
Union: $U_i^j = \cup_{u \in S_i^j} \Gamma_i(u)|$
Distinct neighborhoods: $D_i^j = |\{u: \exists_{v \in S_i^j}, u \in \Gamma_i(v) \subseteq \neg \exists_{v \neq q \in S_i^j}, u \in \Gamma_i(q)\}|$
Mixed neighborhoods: $M_i^j = U_i^j - I_i^j - D_i^j$ The "distinct neighborhoods" feature accounts for all nodes that are significantly correlated to exactly one metabolite within a pathway j. The "mixed neighborhoods" feature accounts for all nodes that are significantly correlated to more than one metabolite within a pathway j, but not all of them. These two features are reminiscent of symmetric difference as defined in set theory. In fact, for two nodes, the "distinct neighborhoods" feature is equal to the size of the symmetric difference of their neighborhoods. However, for a larger number of nodes both features are different from the symmetric difference.

The complete list of 148 features is shown in Table 1, below. The three CNs examined (corresponding to the three harvesting seasons I, II, and III) exhibited different topologies and thus, different feature vectors. These vectors were combined into a single feature vector of 444 features (148×3 networks).

Mapping Metabolic Pathways to Metabolite Correlation Networks

Figure 2:
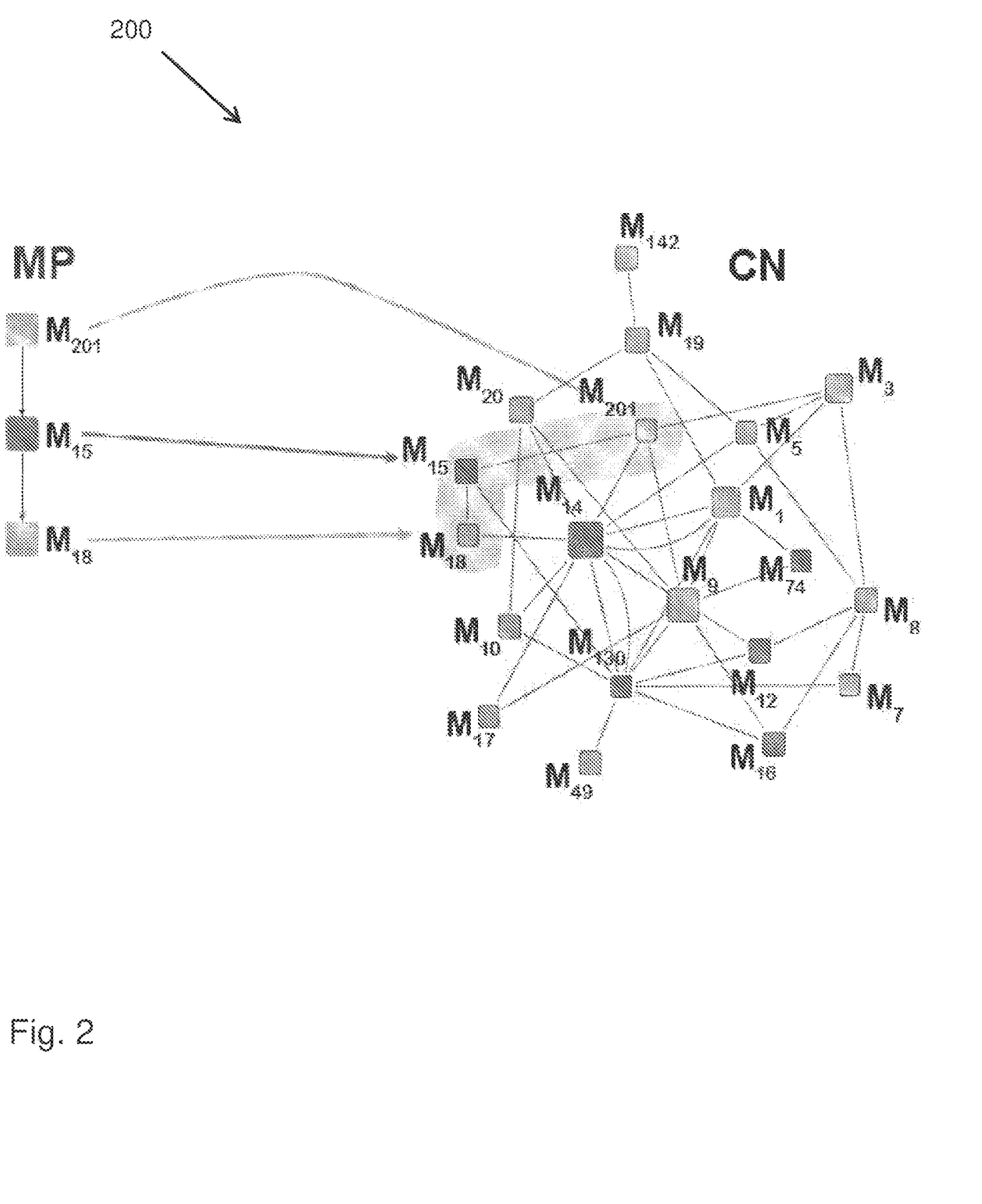
FIG. 2 is a network diagram, depicting a process of mapping metabolic pathways to a metabolite correlation network, according to some embodiments of the present invention.

FIG. 2 is a network diagram, schematically depicting a mapping process 200. Process 200 indicates the format of implementing steps 24 and 30 of process 20, described above with respect to FIG. 1. As indicated in the figure, metabolic pathways are mapped as subgraphs onto the CNs. In mapping, each metabolite of a given metabolic pathway is associated with the node position of the metabolite in the metabolite network. The network features of the resulting subgraph can then be calculated a feature vector of the subgraph, which is the pathway feature vector.

Two types of subgraphs may be considered: conjunctive subgraphs and extended subgraphs. Conjunctive subgraphs included all nodes in $S_i^j$ and links between them, denoted as $SG_i^j = (S_i^j, \{(u,v) \in E_i : u \in S \wedge v \in S\}, w)$. Extended subgraphs included all nodes in $S_i^j$ as well as all of their neighbors, denoted as $ESG_i^j = (V', E', w_i)$, where $V' = \cup_{v \in S_i^j} \Gamma_i(v)$ and $E' = \{(u, v) \in E_i : u, v \in V'\}$. Network features (diameter, diameter centrality, global clustering coefficient, assortativity, density) computed on these two types of subgraphs may be used to describe the pathways. In addition, all features related to the centrality of nodes and links may be computed on the conjunctive subgraph.

The dataset analyzed included 339 pathways mapped to the CNs, for which the 444 features were computed. A large number of features may impair the ability of a machine learning model to generalize beyond the data points used to produce it, a phenomenon known as overfitting. To avoid overfitting and to identify the most contributing features, we selected the features with the highest information gain. This procedure reduces the entropy of the class variable, after analyzing the value for a given feature, as described by Yang, Y. & Pedersen, J. O., "Proceedings of ICML-97, 14th International Conference on Machine Learning," (ed. D. H. Fisher) pp. 412-420 (1997). In the tomato plant study, an InfoGain algorithm was used to rank the contribution of the features to machine learning models. A reduced model, composed of the 20 most highest ranking features according to the InfoGain algorithm, was then used as the model to run predictions of subsequent analysis (see Table 2, below). Feature reduction was performed using the Weka software package (version 3.6.11), described by Hall, M. et al. The WEKA Data Mining Software: An Update. *SIGKDD Explorations* 11 (2009). All of the features were computed using the igraph package34 and standard libraries in R 35 (statistics software available at: https://www.r-project.org/).

Generating and Validating Supervised Machine Learning Models

To identify a machine learning (ML) algorithm appropriate for classifying previously unidentified metabolic pathways in the target organism (i.e., tomato plant), several types of ML algorithms may be tested, such as: random forest (RF), random forest with reduced feature set (RF red), AdaBoost (AB), random tree (RT), support vector machine (SVM), and naïve Bayes (nB). ML algorithm tuning (also referred to as "hyper-parameter optimization") was performed by a trial-and-error approach.

Given an instance whose class is unknown, a trained ML model assigns a probability of that instance being positive (a tomato pathway) or negative (a non-tomato pathway). If the probability of an instance having a positive class is above a predefined threshold, then the predicted class of that instance is positive. Standard performance metrics can be used to compare the predicted classes assigned to the pathways vs. their true classes, i.e., the true positive rate (TPR, recall), false positive rate (FPR), precision, and F-measure. In addition, the performance of ML models can be described by the receiver operating characteristic (ROC) curve, which is created by plotting the TPR as a function of the FPR at different threshold levels. An area under the ROC curve (AUC) of '1' indicates a perfect classifier. The AUC measure of model performance is advantageous because it does not require specifying a threshold and it is independent of the proportion of positive and negative instances in the dataset.

Several procedures may be used to evaluate the ability of an ML model to predict the class of previously unseen instances. In the k-fold, cross-validation method, a dataset is divided into k subsets, each with the same number of instances. Each subset is then removed from the dataset in turn. An ML model is trained based on the remaining subsets. The trained model is applied to every instance in the removed subset, and the predicted class is recorded. After k iterations all instances in the dataset have been assigned a predicted class as opposed to their original true class. Cross-validation is typically used to prove the stability of a given ML algorithm and to assess whether or not the trained model is prone to overfitting. On the one hand, a larger number of folds results in a larger number of instances in the training set during each iteration and consequently renders more accurate models. On the other hand, a larger k requires training more ML models during the evaluation, which increases the computational resources required.

Due to the large number of ML algorithms evaluated for the tomato pericarp study, 10-fold cross-validation was used to select the best ML algorithm. Once the best ML algorithm was chosen, the number of folds was increased to the maximal possible value (339 pathways in our case) in order to obtain the most accurate in silico evaluation results. This special case of k-fold cross validation is known as leave-one-out cross-validation (LOOCV).

All ML modeling and testing was performed using Weka40 software, version 3.6.11. For the current study, the best model was achieved using the random forest algorithm and an equal distribution between MetaCyc and randomly engineered pathways. The random forest model was run with 100 trees, each constructed while considering nine random features, and an out-of-bag error of 0.1711. The random forest algorithm is an ensemble of generated decision trees for which the average prediction of the individual trees is produced. The random forest algorithm for all seasons combined rendered the best AUC result of all models, achieving an AUC of 0.932 (see Table 3, below). The model also had an accuracy of 83.78% (284 correctly vs. 55 incorrectly classified instances).

Out of the 589 TomatoCyc pathways investigated in this study, 169 pathways were identified within each of the three CNs. These pathways were used as the positive instances of the training set.

ML models perform best when they are trained using a balanced training set where there is an equal number of positive and negative instances. In order to tackle this bias "non-pathways" (i.e., randomly generated sets of 2-18 metabolites) were added to the dataset as negative instances. Therefore, all of the positive instances were used for training, along with 85 randomly selected MetaCyc pathways and the same number of randomly selected non-pathways. In total, 170 negative instances were produced.

Sensitivity analysis was performed on the selected ML model, where a subset with 80% of the training set instances was randomly chosen to recreate a model with identical settings. After each model generation, test set instances were subjected to prediction. This analysis was performed with 100 iterations, after which the corresponding average and variance values were computed. If the average value of the sensitivity test corresponded to the value of the original model (greater or smaller than the threshold), the prediction was considered valid. The variance values were used as an indicator of goodness of the prediction value. All but one prediction value yielded valid predictions.

Applying Selected Machine Learning Model

After validation, the feature vectors of the abovementioned 33 plant pathways (which shared at least two compounds with the tomato metabolite CNs), and the remaining 66 MetaCyc pathways that were not included in the training set, were classified by the trained ML model. Prediction values associated with these instances ranged from 0 to 1. The metabolic pathway corresponding to each feature vector was then classified (i.e., predicted) as either positive or negative, at a threshold level of 0.5. That is, unknown metabolic pathways scoring a prediction value greater than the threshold were classified as positively predicted (see Table 4, below).

In total, 22 pathways obtained a prediction value of 0.5 or greater. Of these pathways, six were associated with PlantCyc pathways and 16 with MetaCyc pathways. The β-alanine degradation I pathway achieved the highest prediction value of 0.89. For the PlantCyc pathways, the melibiose degradation pathway achieved the highest prediction value of 0.68.

While the inspection of the relative distribution of the 20 features revealed many differences between positively and negatively predicted metabolic pathways, three features emphasized the difference in particular: the edge betweenness community of subgraph of season II showed higher values for the majority of the positively predicted metabolic pathways, indicating a greater edge betweenness for their corresponding subgraphs; for the weighted standard deviation local clustering coefficient of subgraph within graph feature of season III positively predicted metabolic pathways demonstrated a normal distribution, while negatively predicted metabolic pathways showed a bimodal, left-skewed distribution, suggestive for a greater variety of the local clustering coefficient of subgraphs of non-tomato predicted pathways; the leading eigenvector community of subgraph of season I illustrated a left-skewed distribution for the positively predicted metabolic pathways, showing that they tend to group themselves following a leading eigenvector community.

Sensitivity analysis of the reduced feature model demonstrated that out of the 22 metabolic pathways with a prediction value≥0.5, only one metabolic pathway was misclassified, namely the MetaCyc listed superpathway of histidine, purine, and pyrimidine biosynthesis. Out of the 77 metabolic pathways with a prediction value<0.5, 20.77% were misclassified.

In Vivo Pathway Verification

Frozen pericarp tissue powder was extracted in chloroform-methanol, and metabolites were quantified by gas chromatography-mass spectrometry (GC-MS) following a procedure optimized for tomato tissue, as described at Roessner-Tunali, U. et al., "Metabolic profiling of transgenic tomato plants overexpressing hexokinase reveals that the influence of hexose phosphorylation diminishes during fruit development," *Plant Physiol.*, 133(1), 84-99 (2003). Pure standard of melibiose (purchased from Sigma) was diluted in methanol and run in different quantities to build calibration curves. In the standard, two peaks were identified (1MEOX) (8TMS) main-product and by-product (C37H89NO11Si8) MW 948 RI 2837 and 2868 by library RT 41.8 and 42.1 min. Extract sample (300 μL) was injected (1 μL) with and without spiked-in standard. Identification and annotation of melibiose was achieved based on a comparison to an authentic standard. In addition, control samples with spiked-in non-labeled standards were also used to confirm coelution. Metabolite identity was further matched against publically available databases, in particular the Golm Metabolome Database for GC-MS reference data at http://gmd.mpimp-golm.mpg.de. A similar approach was followed for galactose and glucose.

In addition, PCR amplification was performed on tomato genes Solyc01g10680, Solyc12g006450, Solyc06g071640, Solyc01g088170, Solyc11g071600, and Solyc09g064430, in DNA extracted from tomato fruits. Amplicons are visible (M—1Kb+DNA ladder). These include: genes corresponding to β-alanine degradation I pathway; genes corresponding to the L-tryptophan degradation VII (via indole-3-pyrtruvate) MP; genes corresponding to the β-alanine biosynthesis III pathway.

It is to be understood that all or part of a process and of a system implementing the process of the present invention may be implemented in digital electronic circuitry, or in computer hardware, firmware, software, or in combinations thereof. All or part of the process and system may be implemented as a computer program product, tangibly embodied in an information carrier, such as a machine-readable storage device or in a propagated signal, for execution by, or to control the operation of, data processing apparatus, such as a programmable processor, computer, or deployed to be executed on multiple computers at one website or distributed across multiple websites. Memory storage may also include multiple distributed memory units, including one or more types of storage media. Examples of storage media include, but are not limited to, magnetic media, optical media, and integrated circuits. A computer configured to implement the process may access, provide, transmit, receive, and modify information over wired or wireless networks. The computing may have one or more processors and one or more network interface modules. Processors may be configured as a multi-processing or distributed processing system. Network interface modules may control the sending and receiving of data packets over networks.

It is to be further understood that the scope of the present invention includes variations and modifications thereof which would occur to persons skilled in the art upon reading the foregoing description and which are not disclosed in the prior art.

Tables

TABLE 1

148 Network Features of Feature Vector

| | |
|---|---|
| 1 | as sortativity subgraph |
| 2 | average absolute weighted degree |
| 3 | average absolute weighted degree graph |
| 4 | average closeness centrality graph subgraph |
| 5 | average closeness centrality subgraph |
| 6 | average degree |
| 7 | average degree graph |
| 8 | average edge betweenness subgraph |
| 9 | average geodesic distance graph |
| 10 | average geodesic distance subgraph |
| 11 | average jaccard coefficient |
| 12 | average local clustering coefficient subgraph |
| 13 | average local clustering coefficient subgraph graph |
| 14 | average node betweenness subgraph |
| 15 | average stress centrality |
| 16 | average weighted degree |
| 17 | average weighted degree graph |
| 18 | average weighted geodesic distance graph |
| 19 | average weighted geodesic distance subgraph |
| 20 | common neighborhood |
| 21 | density subgraph |
| 22 | diameter subgraph |
| 23 | diameter through subgraph |
| 24 | distinct neighborhood |
| 25 | edge betweenness community subgraph |
| 26 | edge betweenness community weighted subgraph |
| 27 | edge number |
| 28 | edge number graph |
| 29 | fast greedy community subgraph |
| 30 | fast greedy community weighted subgraph |
| 31 | friends measure graph average |
| 32 | friends measure graph kurtosis |
| 33 | friends measure graph sd |
| 34 | friends measure graph skewness |
| 35 | friends measure graph sum |
| 36 | friends measure subgraph average |
| 37 | friends measure subgraph sd |
| 38 | friends measure subgraph skewness |
| 39 | friends measure subgraph sum |
| 40 | friends mesure subgraph kurtosis |
| 41 | geodesic distance graph |
| 42 | geodesic distance subgraph |
| 43 | geodesic distance weighted graph |
| 44 | geodesic distance weighted subgraph |
| 45 | global clustering coefficient subgraph |

TABLE 1-continued

148 Network Features of Feature Vector

| | |
|---|---|
| 46 | group betweenness subgraph |
| 47 | jaccard coefficient |
| 48 | kurtosis absolute weighted degree |
| 49 | kurtosis absolute weighted degree graph |
| 50 | kurtosis closeness centrality graph subgraph |
| 51 | kurtosis degree |
| 52 | kurtosis degree graph |
| 53 | kurtosis edge betweenness subgraph |
| 54 | kurtosis geodesic distance graph |
| 55 | kurtosis geodesic distance subgraph |
| 56 | kurtosis jaccard coefficient |
| 57 | kurtosis local clustering coefficient subgraph |
| 58 | kurtosis local clustering coefficient subgraph graph |
| 59 | kurtosis node betweenness subgraph |
| 60 | kurtosis stress centrality |
| 61 | kurtosis weighted degree |
| 62 | kurtosis weighted degree graph |
| 63 | kurtosis weighted geodesic distance graph |
| 64 | kurtosis weighted geodesic distance subgraph |
| 65 | kurtsos cloeseness centrality subgraph |
| 66 | label propagation community subgraph |
| 67 | label propagation community weighted subgraph |
| 68 | leading eigentvector community subgraph |
| 69 | leading eigenvector community weighted subgraph |
| 70 | mixed neighborhood |
| 71 | multilevel community subgraph |
| 72 | multilevel community weighted subgraph |
| 73 | preferential attachment score |
| 74 | sd absolute weighted degree |
| 75 | sd absolute weighted degree graph |
| 76 | sd closeness centrality graph subgraph |
| 77 | sd closeness centrality subgraph |
| 78 | sd degree |
| 79 | sd degree graph |
| 80 | sd edge betweenness subgraph |
| 81 | sd geodesic distance graph |
| 82 | sd geodesic distance subgraph |
| 83 | sd jaccard coefficient |
| 84 | sd local clustering coefficient subgraph |
| 85 | sd local clustering coefficient subgraph graph |
| 86 | sd node betweenness subgraph |
| 87 | sd stress centrality |
| 88 | sd weighted degree |
| 89 | sd weighted degree graph |
| 90 | sd weighted geodesic distance graph |
| 91 | sd weighted geodesic distance subgraph |
| 92 | skewness absolute weighted degree |
| 93 | skewness absolute weighted degree graph |
| 94 | skewness closeness centrality graph subgraph |
| 95 | skewness closeness centrality subgraph |
| 96 | skewness degree |
| 97 | skewness degree graph |
| 98 | skewness edge betweenness subgraph |
| 99 | skewness geodesic distance graph |
| 100 | skewness geodesic distance subgraph |
| 101 | skewness jaccard coefficient |
| 102 | skewness local clustering coefficient subgraph |
| 103 | skewness local clustering coefficient subgraph graph |
| 104 | skewness node betweenness subgraph |
| 105 | skewness stress centrality |
| 106 | skewness weighted degree |
| 107 | skewness weighted degree graph |
| 108 | skewness weighted geodesic distance graph |
| 109 | skewness weighted geodesic distance subgraph |
| 110 | total absolute weighted degree |
| 111 | total absolute weighted degree graph |
| 112 | total weighted degree |
| 113 | total weighted degree graph |
| 114 | union of neighborhood |
| 115 | walktrap community subgraph |
| 116 | walktrap community weighted subgraph |
| 117 | weighted average closeness centrality graph subgraph |
| 118 | weighted average closeness centrality subgraph |
| 119 | weighted average edge betweeness subgraph |
| 120 | weighted average local clustering coefficient subgraph |
| 121 | weighted average local clustering coefficient subgraph graph |
| 122 | weighted average node betweenness subgraph |
| 123 | weighted average stress centrality |

TABLE 1-continued

148 Network Features of Feature Vector

| | |
|---|---|
| 124 | weighted diameter subgraph |
| 125 | weighted diameter through subgraph |
| 126 | weighted global clustering coefficient subgraph |
| 127 | weighted group betweenness subgraph |
| 128 | weighted kurtosis closeness centrality graph subgraph |
| 129 | weighted kurtosis closeness centrality subgraph |
| 130 | weighted kurtosis edge betweenness subgraph |
| 131 | weighted kurtosis local clustering coefficient subgraph |
| 132 | weighted kurtosis local clustering coefficient subgraph graph |
| 133 | weighted kurtosis node betweenness subgraph |
| 134 | weighted kurtosis stress centrality |
| 135 | weighted sd closeness centrality graph subgraph |
| 136 | weighted sd closeness centrality subgraph |
| 137 | weighted sd edge betweenness subgraph |
| 138 | weighted sd local clustering coefficient subgraph |
| 139 | weighted sd local clustering coefficient subgraph graph |
| 140 | weighted sd node betweenness subgraph |
| 141 | weighted sd stress centrality |
| 142 | weighted skewness closeness centrality graph subgraph |
| 143 | weighted skewness closeness centrality subgraph |
| 144 | weighted skewness edge betweenness subgraph |
| 145 | weighted skewness local clustering coefficient subgraph |
| 146 | weighted skewness local clustering coefficient subgraph graph |
| 147 | weighted skewness node betweenness subgraph |
| 148 | weighted skewness stress centrality |

TABLE 2

20 features with best predictive ability for study

| Feature | Season | Definition | Mathematical moment |
|---|---|---|---|
| Skewness absolute weighted degree of graph | II | The absolute weighted node degree quantifies the absolute weight of all links incident on a node. In case of correlation-based networks the weight of an link corresponds to the absolute correlation coefficient. Here it denotes all links within the subgraph and the links linking the nodes of the subgraph to the remaining nodes of the graph | skewness |
| Kurtosis absolute weighted degree of graph | II | | kurtosis |
| Absolute weighted degree of graph | II | | — |
| Standard deviation of absolute weighted degree of graph | II | | standard deviation |
| Total absolute weighted degree of graph | II | | Accumulative absolute weighted degree |
| Weighted standard deviation node betweenness centrality of subgraph | II | The weighted node betweenness centrality of a node i is given by the number of weighted geodesic distances between any two nodes that contain node i - here delimited to the subgraph | Standard deviation |
| Edge number of graph | II | Total amount of links incident on adjacent nodes of subgraph including links to the nodes of the remaining graph | — |
| Edge betweenness community of subgraph | II | The edge betweenness community detecting algorithm is based on the edge betweenness centrality property. It applies a hierarchical decomposition process in which links are removed based on their betweenness score. Communities are built based on the idea that links connecting different communities are more likely to be contained as multiple shortest paths. Here a feature is constructed given by the ratio of how many nodes of the subgraph co-reside in the largest community as opposed to nodes that are located within other communities. | — |
| Mixed neighborhoods | II | The mixed neighborhoods feature accounts for all nodes that are significantly correlated to more than one metabolite within a pathway, but not all of them (see definition in Materials and Methods for more details) | — |
| Union of neighborhoods | II | The union of neighborhoods features quantifies how many nodes/friends of order one all nodes within the subgraph have in total, counting each friend only | — |

TABLE 2-continued 20 features with best predictive ability for study

| Feature | Season | Definition | Mathematical moment |
|---|---|---|---|
| | | once in the background of the entire graph and excluding friendship to each other (see definition in Materials and Methods for more details) | |
| Total weighted degree of graph | II | The weighted degree quantifies the weight of all links incident on a node. In case of correlation-based networks the weight of a link corresponds to the correlation coefficient. Here it denotes all links within the subgraph and the links linking the nodes of the subgraph to the remaining nodes of the graph | Accumulative weighted degree |
| Weighted average closeness centrality of subgraph | II | The weighted closeness centrality is the reciprocal of the weighted average path length between a given node i and all other nodes in a given connected graph. Here, the closeness centrality was measured for every node in the subgraph. | Average |
| Average closeness centrality of subgraph | III | The closeness centrality is the reciprocal of the average path length between a given node i and all other nodes in a given connected graph. Here, the closeness centrality was measured for every node in the subgraph. | Average |
| Density of subgraph | I | The density of a graph is the number of links over the number of possible links - here delimited to the subgraph | — |
| Average closeness centrality of subgraph | I | See above | Average |
| Weighted average closeness centrality of subgraph | I | See above | Average |
| Weighted standard deviation local clustering coefficient of subgraph within graph | III | The local clustering coefficient of a node i is the proportion of existing links from all possible links between the neighbors of i, taking into account the weight of edges. It quantifies how close the subnetwork induced by i and its adjacent nodes is from a clique. Here, the local clustering coefficient is estimated for all nodes in the subgraph in the background of the entire graph. | Standard deviation |
| Leading eigenvector community of subgraph | I | The leading eigenvector community detecting algorithm applies a top-down hierarchical approach that optimizes the modularity function. In each step the graph is split into two parts in a way that separation yields a significant increase in modularity. The split is performed by determining the leading eigenvector of the so-called modularity matrix. Here a feature is constructed given by the ratio of how many nodes of the subgraph co-reside in the largest community as opposed to nodes that are located within other communities. | |
| Average closeness centrality of subgraph | II | See above | Average |

TABLE 2-continued 20 features with best predictive ability for study

| Feature | Season | Definition | Mathematical moment |
|---|---|---|---|
| Average weighted degree of graph | II | See above | Average |

TABLE 3

Random forest model performance measure summary

| | Class | True positive rate (Recall) | False positive rate | Precision | F-Measure | AUC |
|---|---|---|---|---|---|---|
| All Season features-model I | TomatoCyc pathways | 0.917 | 0.241 | 0.791 | 0.849 | 0.932 |
| | MetaCyc and random pathways | 0.759 | 0.083 | 0.902 | 0.824 | 0.932 |
| | Weighted average | 0.838 | 0.162 | 0.847 | 0.837 | 0.932 |
| Season I features-Model II | TomatoCyc pathways | 0.864 | 0.182 | 0.825 | 0.844 | 0.918 |
| | MetaCyc and random pathways | 0.818 | 0.136 | 0.858 | 0.837 | 0.917 |
| | Weighted average | 0.841 | 0.159 | 0.841 | 0.841 | 0.917 |
| Season II features-model III | TomatoCyc pathways | 0.876 | 0.229 | 0.791 | 0.831 | 0.91 |
| | MetaCyc and random pathways | 0.771 | 0.124 | 0.862 | 0.814 | 0.91 |
| | Weighted average | 0.823 | 0.177 | 0.827 | 0.823 | 0.91 |
| Season III features-model IV | TomatoCyc pathways | 0.828 | 0.306 | 0.729 | 0.776 | 0.876 |
| | MetaCyc and random pathways | 0.694 | 0.172 | 0.803 | 0.744 | 0.876 |
| | Weighted average | 0.761 | 0.239 | 0.766 | 0.76 | 0.876 |
| Averaged seasons feature-model V | TomatoCyc pathways | 0.858 | 0.212 | 0.801 | 0.829 | 0.914 |
| | MetaCyc and random pathways | 0.788 | 0.142 | 0.848 | 0.817 | 0.914 |
| | Weighted average | 0.823 | 0.177 | 0.825 | 0.823 | 0.914 |
| Reduced features based on model I-model VI | TomatoCyc pathways | 0.858 | 0.188 | 0.819 | 0.838 | 0.923 |
| | MetaCyc and random pathways | 0.812 | 0.142 | 0.852 | 0.831 | 0.923 |
| | Weighted average | 0.835 | 0.165 | 0.836 | 0.835 | 0.923 |

TABLE 4

Pathway existence prediction values, showing sensitivity analysis. A sensitivity analysis average of less than 0.5 is deemed false. All but one of the 22 PlantCyc positively predicted pathways were confirmed by sensitivity analysis.

| Database | Pathway | Original model | Sensitivity analysis average | Sensitivity analysis variance | Conform to original model average |
|---|---|---|---|---|---|
| MetaCyc | beta-alanine degradation I | 0.89 | 0.631 | 0.01812 | TRUE |
| MetaCyc | superpathway of butirocin biosynthesis | 0.85 | 0.914 | 0.00990 | TRUE |
| MetaCyc | isopenicillin N biosynthesis | 0.85 | 0.879 | 0.01379 | TRUE |
| MetaCyc | L-tryptophan degradation VII (via indole-3-pyruvate) | 0.76 | 0.773 | 0.01815 | TRUE |
| MetaCyc | L-tryptophan degradation IV (via indole-3-lactate) | 0.76 | 0.843 | 0.01298 | TRUE |
| MetaCyc | gliotoxin biosynthesis | 0.75 | 0.843 | 0.01298 | TRUE |
| MetaCyc | superpathway of scopolin and esculin biosynthesis | 0.71 | 0.928 | 0.00850 | TRUE |
| PlantCyc | melibiose degradation | 0.68 | 0.534 | 0.08974 | TRUE |
| PlantCyc | beta-alanine biosynthesis III | 0.68 | 0.596 | 0.03190 | TRUE |
| MetaCyc | apicidin F biosynthesis | 0.68 | 0.862 | 0.01167 | TRUE |
| MetaCyc | creatine biosynthesis | 0.68 | 0.796 | 0.02079 | TRUE |
| MetaCyc | mycolyl-arabinogalactan-peptidoglycan complex biosynthesis | 0.65 | 0.708 | 0.02882 | TRUE |

TABLE 4-continued

Pathway existence prediction values, showing sensitivity analysis. A sensitivity analysis average of less than 0.5 is deemed false. All but one of the 22 PlantCyc positively predicted pathways were confirmed by sensitivity analysis.

| Database | Pathway | Original model | Sensitivity analysis average | Sensitivity analysis variance | Conform to original model average |
|---|---|---|---|---|---|
| PlantCyc | putrescine degradation I | 0.63 | 0.749 | 0.02393 | TRUE |
| PlantCyc | hypoglycin biosynthesis | 0.61 | 0.824 | 0.01497 | TRUE |
| MetaCyc | L-tryptophan degradation VIII (to tryptophol) | 0.61 | 0.704 | 0.02038 | TRUE |
| PlantCyc | lathyrine biosynthesis | 0.6 | 0.639 | 0.02321 | TRUE |
| MetaCyc | superpathway of L-methionine salvage and degradation | 0.6 | 0.731 | 0.02034 | TRUE |
| MetaCyc | superpathway of histidine, purine, and pyrimidine biosynthesis | 0.58 | 0.481 | 0.03771 | FALSE |
| MetaCyc | L-glutamate degradation VIII (to propanoate) | 0.54 | 0.571 | 0.03319 | TRUE |
| MetaCyc | L-phenylalanine degradation IV (mammalian, via side chain) | 0.53 | 0.714 | 0.02364 | TRUE |
| PlantCyc | superpathway of aspartate and asparagine biosynthesis | 0.52 | 0.624 | 0.02851 | TRUE |
| MetaCyc | benzoate fermentation (to acetate and cyclohexane carboxylate) | 0.5 | 0.609 | 0.03113 | TRUE |

The invention claimed is:

1. A method for determining a likelihood of a metabolic pathway existing in an organism, implemented by a computer processor having an associated memory, the memory including instructions that when executed by the computer processor implement the method comprising:
calculating a network feature vector for each metabolic pathway of first and second sets of metabolic pathways, wherein the first set is composed of metabolic pathways known to exist in the organism, wherein the second set is composed of metabolic pathways known to not exist in the organism, wherein elements of the network feature vectors are network properties of subgraphs of a metabolite concentration correlation network (MCCN), wherein the MCCN links together nodes representing metabolites of the organism, wherein the links between nodes represent correlations between concentration profiles of the metabolites; wherein each subgraph is a mapping of metabolites of the existing or not existing metabolic pathways to the nodes representing those metabolites in the MCCN;
receiving the calculated network feature vectors at a supervised machine learning (SML) model, to train the SML model for classifying metabolic pathways as existing or not existing in the organism according to network feature vectors determined from MCCN subgraph mappings;
mapping to the MCCN a proposed metabolic pathway to determine a network feature vector of the proposed metabolic pathway, wherein the proposed metabolic pathway is not previously known to exist in the organism; and
processing the network feature vector determined for the proposed metabolic pathway, by the trained SML model, to determine a likelihood of the proposed metabolic pathway existing in the organism.

2. The method of claim 1, further comprising setting a model threshold of the SML model, wherein the likelihood is positive when the SML model indicates a prediction value above the threshold, and the likelihood is negative when the SML model indicates a prediction value below the threshold.

3. The method of claim 2, further comprising performing in vivo testing of the proposed metabolic pathway when the likelihood is positive.

4. The method of claim 1, wherein training the SML model comprises training on at least two machine learning models and selecting a model that provides results having the greatest area under a receiver operating characteristic curve (AUC).

5. The method of claim 4, wherein the machine learning models comprise at least one algorithm from a set including: random forest (RF), random forest with reduced feature set (RF red), AdaBoost (AB), XGBoost, random tree (RT), support vector machine (SVM), and naïve Bayes (nB) algorithms.

6. The method of claim 1, wherein the network feature vectors include highest ranking features according to an InfoGain algorithm.

7. The method of claim 1, wherein training the SML model comprises applying the network feature vectors of the first and second sets of metabolic pathways to train a first SML model, determining a subset of features of the network feature vectors that most contribute to the classifying capability of the first SML model, and training a second SML model by applying network feature vectors of the first and second sets that include only the subset of features determined to contribute the most to the classifying capability.

8. The method of claim 7, wherein the subset of features are the features listed in Table 2 of the specification.

9. A system for identifying previously unknown metabolic pathways in an organism, comprising a computer processor and an associated memory, the memory comprising instructions that when executed by the computer processor implement steps comprising:
calculating a network feature vector for each metabolic pathway of first and second sets of metabolic pathways, wherein the first set is composed of metabolic pathways known to exist in the organism, wherein the second set is composed of metabolic pathways known to not exist in the organism, wherein elements of the network feature vectors are network properties of subgraphs of a metabolite concentration correlation network (MCCN), wherein the MCCN links together nodes representing metabolites of the organism, wherein the links between nodes represent correlations between concentration profiles of the metabolites; wherein each subgraph is a mapping of metabolites of the existing or not existing metabolic pathways to the nodes representing those metabolites in the MCCN;

receiving the calculated network feature vectors at a supervised machine learning (SML) model, to train the SML model for classifying metabolic pathways as existing or not existing in the organism according to network feature vectors determined from MCCN subgraph mappings;

mapping to the MCCN a proposed metabolic pathway to determine a network feature vector of the proposed metabolic pathway, wherein the proposed metabolic pathway is not previously known to exist in the organism; and processing the network feature vector, determined for the proposed metabolic pathway, by the trained SML model, to determine a likelihood of the proposed metabolic pathway existing in the organism.

* * * * *